(12) United States Patent
Daugirdas (10) Patent No.: US 11,344,655 B2
(45) Date of Patent: May 31, 2022

(54) HOLOGRAPHIC CONTROL SYSTEM FOR HEMODIALYSIS

(71) Applicant: John T. Daugirdas, Burr Ridge, IL (US)

(72) Inventor: John T. Daugirdas, Burr Ridge, IL (US)

( * ) Notice: Subject to any disclaimer, the term of this patent is extended or adjusted under 35 U.S.C. 154(b) by 79 days.

(21) Appl. No.: 16/914,588

(22) Filed: Jun. 29, 2020

(65) Prior Publication Data

US 2021/0402069 A1 Dec. 30, 2021

(51) Int. Cl.
*A61M 1/16* (2006.01)
*G02B 5/32* (2006.01)

(52) U.S. Cl.
CPC ........ *A61M 1/1601* (2014.02); *A61M 1/1621* (2014.02); *G02B 5/32* (2013.01); *A61M 2205/3553* (2013.01); *A61M 2205/505* (2013.01); *A61M 2205/583* (2013.01)

(58) Field of Classification Search
CPC .............. A61M 1/1601; A61M 1/1621; A61M 2205/3553; A61M 2205/505; A61M 2205/583; G02B 5/32
See application file for complete search history.

(56) References Cited

U.S. PATENT DOCUMENTS

| | | | |
|---|---|---|---|
| 5,326,476 A | 7/1994 | Grogan et al. | |
| 6,377,238 B1 | 4/2002 | McPheters | |
| 7,054,045 B2 | 5/2006 | McPheters et al. | |
| 7,259,899 B2 | 8/2007 | Ciaudelli et al. | |
| 8,218,213 B2 | 7/2012 | Ciaudelli et al. | |
| 8,908,249 B2 | 12/2014 | Ciaudelli et al. | |
| 2007/0016008 A1 | 1/2007 | Schoenefeld | |
| 2009/0109175 A1 | 4/2009 | Fein et al. | |
| 2009/0184851 A1 | 7/2009 | Grego et al. | |
| 2011/0249309 A1 | 10/2011 | McPheters et al. | |
| 2013/0096575 A1 | 4/2013 | Olson | |
| 2015/0097777 A1 | 4/2015 | Brown et al. | |

OTHER PUBLICATIONS

Holographic controls may be wave of the future; Kiosk Marketplace; https://www.kioskmarketplace.com/articles/holographic-controls-may-be-wave-of-the-future/; retrieved on Jun. 28, 2021; 10 pages.
Holotouch; https://holotouch.com/; retrieved on Jun. 28, 2021; 1 page.
Holotouch® Technology applied to your Product; Holotouch; https://holotouch.com/working-with-holotouch/holotouch-applications/; retrieved on Jun. 28, 2021; 1 page.
International Search Report; International Searching Authority; International Patent Application No. PCT/US2021/039383; dated Oct. 4, 2021; 2 pages.
Written Opinion of the International Searching Authority; International Searching Authority; International Patent Application No. PCT/US2021/039383; dated Oct. 4, 2021; 6 pages.
Elevator in China uses holographic buttons amid coronavirus outbreak; South China Morning Post; https://www.scmp.com/print/abacus/news-bites/article/3073998/elevator-china-uses-holographic-buttons-amid-coronavirus-outbreak; retrieved on Jun. 30, 2020; 3 pages.

*Primary Examiner* — Dirk R Bass
(74) *Attorney, Agent, or Firm* — Taft Stettinius & Hollister LLP (57) ABSTRACT

A system for holographic control of a hemodialysis machine according to one embodiment includes a hemodialysis control system of the hemodialysis machine and a holographic system communicatively coupled to the hemodialysis control system.

19 Claims, 3 Drawing Sheets

HOLOGRAPHIC CONTROL SYSTEM FOR HEMODIALYSIS

BACKGROUND

Frequently touched surfaces during a medical treatment of a patient pose a significant risk of touch contamination. As such, various safeguards and procedures are routinely implemented in order to ensure patients and healthcare professionals remain minimally exposed to any threatening surface-residing bacteria and/or viruses, while reducing the risk of spread and further contamination. For example, in a hemodialysis treatment setting, healthcare professionals wear disposable gloves while modifying treatment settings/parameters on a touch screen of a hemodialysis machine and discard those gloves after interacting with machine and/or the patient. Each time the healthcare professional interacts with the hemodialysis machine (even if only briefly), she must don, doff, and discard a new pair of disposable gloves, thereby consuming significant amounts of time and effort throughout an entire work shift, where she will have many patient interactions with several patients.

SUMMARY

One embodiment is directed to a unique system, components, and methods for holographic control of a hemodialysis machine. Other embodiments are directed to apparatuses, systems, devices, hardware, methods, and combinations thereof for holographic control of a hemodialysis machine.

According to an embodiment, a system for holographic control of a hemodialysis machine may include a hemodialysis control system of the hemodialysis machine, wherein the hemodialysis control system comprises at least one first processor and at least one first memory comprising a first plurality of instructions stored thereon that, in response to execution by the at least one first processor, causes the hemodialysis control system to provide a first user interface of the hemodialysis machine, and a holographic system communicatively coupled to the hemodialysis control system, wherein the holographic system comprises at least one second processor and at least one second memory comprising a second plurality of instructions stored thereon that, in response to execution by the at least one second processor, causes the holographic system to display a virtual three-dimensional image representative of a second user interface for the hemodialysis machine.

In some embodiments, the first user interface and the second user interface may be configured to control a same set of functions of the hemodialysis machine.

In some embodiments, the first user interface may include a first set of user interface components and the second user interface may include a second set of user interface components identical to the first set of user interface components.

In some embodiments, the first user interface may include a first set of user interface components and the second user interface may include a second set of user interface components different from the first set of user interface components.

In some embodiments, the holographic system may be communicatively coupled to the hemodialysis control system via a wired communication port of the hemodialysis control system.

In some embodiments, the hemodialysis control system may include an Ethernet port, and the holographic system may be communicatively coupled to the hemodialysis control system via the Ethernet port.

In some embodiments, the hemodialysis control system may include a USB port, and the holographic system may be communicatively coupled to the hemodialysis control system via the USB port.

In some embodiments, the hemodialysis control system may include a serial communication port, and the holographic system may be communicatively coupled to the hemodialysis control system via the serial communication port.

In some embodiments, the holographic system may be communicatively coupled to the hemodialysis control system via a wireless communication connection directly between the holographic system and the hemodialysis control system.

In some embodiments, the wireless communication connection may be a Bluetooth communication connection between the holographic system and the hemodialysis control system.

In some embodiments, the hemodialysis control system may include a touchscreen display that provides the first user interface of the hemodialysis machine.

In some embodiments, the system may further include a remote computing system communicatively coupled to the hemodialysis control system via a network and configured to receive patient treatment data from the hemodialysis control system.

According to another embodiment, a system for holographic control of a medical device at risk of touch contamination may include a control system of the medical device, wherein the control system comprises at least one first processor and at least one first memory comprising a first plurality of instructions stored thereon that, in response to execution by the at least one first processor, causes the control system to provide a first user interface of the medical device, and a holographic system communicatively coupled to the control system, wherein the holographic system comprises at least one second processor and at least one second memory comprising a second plurality of instructions stored thereon that, in response to execution by the at least one second processor, causes the holographic system to display a virtual three-dimensional image representative of a second user interface for the medical device.

In some embodiments, the medical device may assist with hemodialysis of a patient.

In some embodiments, the first user interface and the second user interface may be configured to control a same set of functions of the medical device.

In some embodiments, the first user interface may include a first set of user interface components and the second user interface may include a second set of user interface components identical to the first set of user interface components.

In some embodiments, the first user interface may include a first set of user interface components and the second user interface may include a second set of user interface components different from the first set of user interface components.

In some embodiments, the control system may include at least one of an Ethernet port, a USB port, or a serial communication port, and the holographic system may be communicatively coupled to the control system via one of the at least one of the Ethernet port, the USB port, or the serial communication port.

In some embodiments, the holographic system may be communicatively coupled to the control system via a wireless communication connection directly between the holographic system and the control system.

According to yet another embodiment, a system for holographic control of a hemodialysis machine may include a hemodialysis control system of the hemodialysis machine, and a holographic system communicatively coupled to the hemodialysis control system.

Further embodiments, forms, features, and aspects of the present application shall become apparent from the description and figures provided herewith.

BRIEF DESCRIPTION OF THE DRAWINGS

The concepts described herein are illustrative by way of example and not by way of limitation in the accompanying figures. For simplicity and clarity of illustration, elements illustrated in the figures are not necessarily drawn to scale. Where considered appropriate, references labels have been repeated among the figures to indicate corresponding or analogous elements.

DETAILED DESCRIPTION

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described. Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

The disclosed embodiments may, in some cases, be implemented in hardware, firmware, software, or a combination thereof. The disclosed embodiments may also be implemented as instructions carried by or stored on one or more transitory or non-transitory machine-readable (e.g., computer-readable) storage media, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures unless indicated to the contrary. Additionally, the inclusion of a structural or method feature in a particular figure is not meant to imply that such feature is required in all embodiments and, in some embodiments, may not be included or may be combined with other features.

Figure 1:
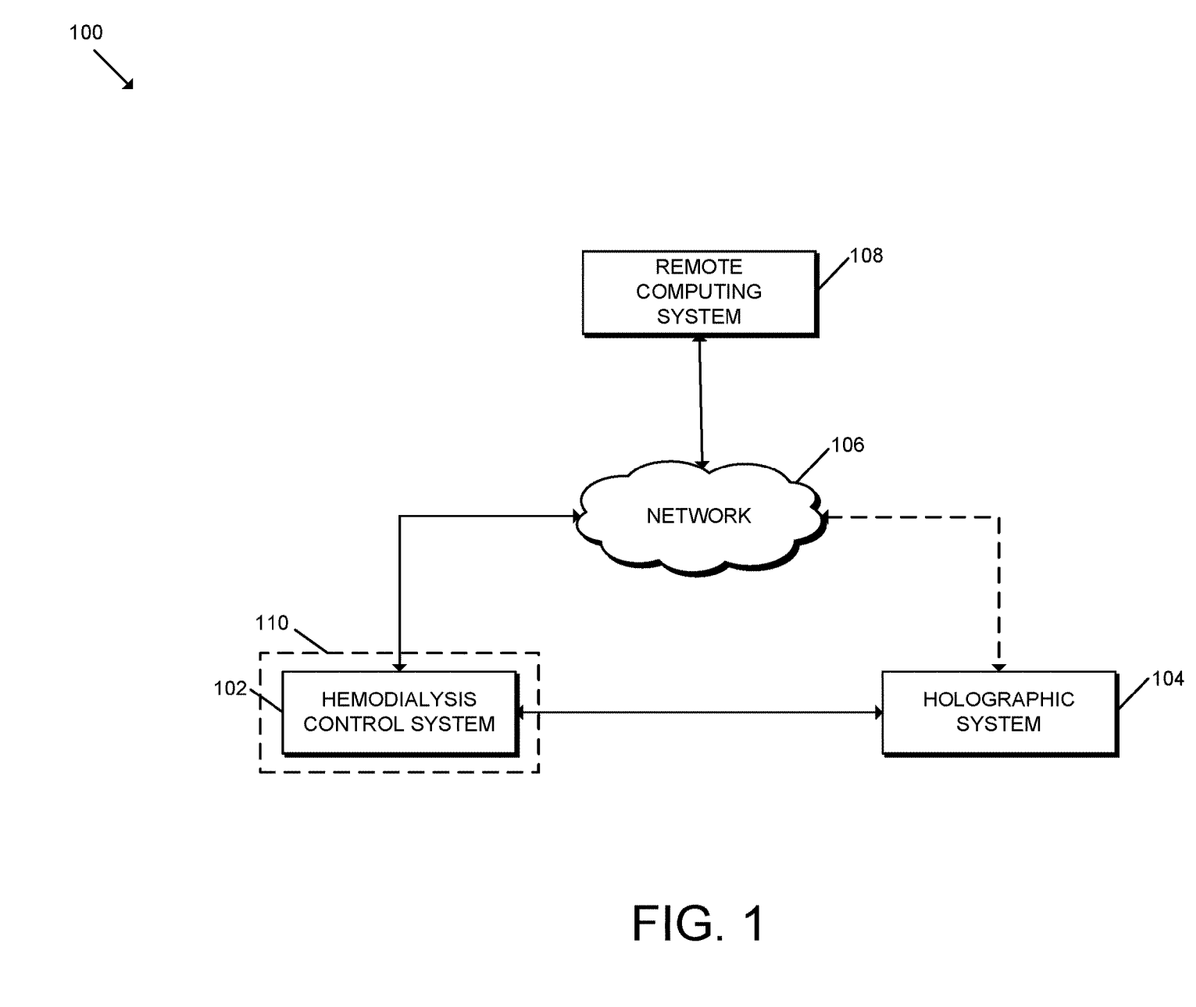
FIG. 1 is a simplified block diagram of at least one embodiment of a system for holographic control of a hemodialysis machine during the treatment of a patient.

Referring now to FIG. 1, in the illustrative embodiment, a system 100 for holographic control of a hemodialysis machine 110 includes a hemodialysis control system 102, a holographic system 104, a network 106, and a remote computing system 108. As described in detail below, the system 100 allows healthcare professionals to adjust settings/parameters on a hemodialysis machine 110 without risking touch contamination and without donning/doffing a new pair of disposable gloves. In particular, in the illustrative embodiment, the holographic system 104 is communicatively coupled to the hemodialysis control system 102 and configured to provide a contactless user interface with parallel controls for the hemodialysis machine 110. In other words, the holographic interface does not require touching any surface of the machine 110 or the physical components of the holographic system 104. The holographic interface allows for contactless initiating and/or changing operating parameters of the hemodialysis machine 110, obviating the need for hand hygiene and glove changes after effecting the change in operating parameters.

The hemodialysis control system 102 forms a portion of or is otherwise associated with a hemodialysis machine 110 and configured to control the operations of the machine 110 as described in further detail below. It should be appreciated that the hemodialysis machine 110 that includes and/or is associated with the hemodialysis control system 102 may be embodied as any type of machine capable of performing extracorporeal dialysis or filtration of blood of a patient (e.g., as part of a dialysis treatment for patients suffering from renal insufficiencies). As described herein, the hemodialysis control system 102 may be used by a healthcare professional to initially configure a hemodialysis machine 110 for a patient's dialysis treatment, which may include providing patient-specific information, treatment parameters, and/or other settings/information to the hemodialysis control system 102 of the hemodialysis machine 110. Further, the healthcare professional may adjust various settings of the machine 110 throughout the treatment based on various conditions. For example, in some circumstances, the healthcare professional may change the blood flow rate and/or ultrafiltration rate of the machine 110 using an interface of the hemodialysis control system 102. In other circumstances, the healthcare professional may use an interface of the hemodialysis control system 102 to put the machine 110 into and/or revert the machine 110 from a bypass mode in which the dialysate is routed around the dialyzer of the machine 110. Further, in various circumstances, an alarm may be triggered due to one or more thresholds being surpassed (e.g., a high blood pressure threshold, a low blood pressure threshold, etc.). In such circumstances, the healthcare professional may use the interface of the hemodialysis control system 102 to clear the alarm and/or adjust one or more settings of the machine 110. Although the control system 102 is described herein as being associated with a hemodialysis machine 110, it should be appreciated that, in other embodiments, the control system 102 may be configured to control another type of medical device or equipment where touch contamination and/or infection is a concern. As such, the relevant technologies described herein may be employed in conjunction with another type of medical device or equipment in those embodiments.

The holographic system 104 may be embodied as any type of device or collection of devices capable of rendering one or more holographic images (i.e., virtual three-dimensional images) and sensing/interpreting human interaction with the holographic image(s). In the illustrative embodiment, the holographic system 104 provides an additional or alternative holographic user interface for the hemodialysis control system 102 or, more generally, the hemodialysis machine 110. It should be appreciated that, in some embodiments, the user interface features of the holographic system 104 may parallel/mirror those of the hemodialysis control system 102 itself or a portion thereof (e.g., have the same inputs/outputs as a primary touchscreen of the hemodialysis control system 102), whereas in other embodiments, the user interface features of the holographic system 104 may be different from those of the hemodialysis control system 102 (e.g., a superset of features, a subset of features, additional/alternative features, etc.).

Depending on the particular embodiment, the holographic system 104 may be communicatively coupled to the hemodialysis control system 102 via one or more wired and/or wireless communication connections. For example, in some embodiments, the holographic system 104 may be communicatively coupled to the hemodialysis control system 104 via the communication circuitry 314 of the hemodialysis control system 102 described in further detail below. As such, it should be appreciated that the holographic system 104 may include communication circuitry similar to the communication circuitry 314 of the hemodialysis control system 102 in some embodiments.

In some embodiments, the hemodialysis control system 102 may be communicatively coupled to a remote computing system 108 via a network 106. It should be appreciated that the remote computing system 108 may be embodied as any type of device or collection of devices suitable for communicating with the hemodialysis control system 102 regarding the treatment of a patient and/or otherwise (e.g., software/firmware updates on the control system 102). For example, in various embodiments, the remote computing system 108 may be embodied as an electronic medical records system, nurse station computing device, and/or other relevant computing system. Depending on the particular embodiment, the communication connection between the hemodialysis system 102 and the remote computing system 108 may be wired and/or wireless. Further, in some embodiments, the holographic system 104 may be configured to communicate with the remote computing system 108 via the network 106 (e.g., wirelessly).

It should be further appreciated that, in some embodiments, the remote computing system 108 may be embodied as a virtual computing environment residing "on" a computing system (e.g., a distributed network of devices) in which various virtual functions (e.g., Lambda functions, Azure functions, Amazon Web Services cloud functions, Google cloud functions, and/or other suitable virtual functions) may be executed corresponding with the functions of the remote computing system 108 described herein. For example, when an event occurs (e.g., data is transferred to the remote computing system 108 for handling), the virtual computing environment may be communicated with (e.g., via a request to an API of the virtual computing environment), whereby the API may route the request to the correct virtual function (e.g., a particular server-ambiguous computing resource) based on a set of rules. As such, when a request for the transmission of particular data is made (e.g., via an appropriate interface to the remote computing system 108), the appropriate virtual function(s) may be executed to perform the actions before eliminating the instance of the virtual function(s).

The network 106 may be embodied as any type of communication network(s) capable of facilitating communication between the various devices of the system 100. As such, the network 106 may include one or more networks, routers, switches, computers, and/or other intervening devices. For example, the network 106 may be embodied as or otherwise include one or more cellular networks, telephone networks, local or wide area networks, publicly available global networks (e.g., the Internet), ad hoc networks, long-range wireless communication networks, or a combination thereof.

It should be appreciated that the remote computing system 108 may be embodied as a computing device similar to the computing device 200 described below in reference to FIG. 2. For example, in the illustrative embodiment, the remote computing system 108 includes a processing device 202 and a memory 206 having stored thereon operating logic 208 for execution by the processing device 202 for operation of the corresponding device. Additionally, it should be appreciated that each of the hemodialysis control system 102 and the holographic system 104 may include features similar to the features described below in reference to the computing device 200 of FIG. 2 (e.g., the processing device 202, the I/O 204, the memory 206, and/or the operating logic 208).

Although only one hemodialysis control system 102, one holographic system 104, and one remote computing system 108 are shown in the illustrative embodiment of FIG. 1, the system 100 may include multiple hemodialysis control systems 102, holographic systems 104, and/or remote computing systems 108 in other embodiments. For example, in some embodiments, a single remote computing system 108 may be configured to receive patient treatment information from multiple hemodialysis control systems 102.

Figure 2:
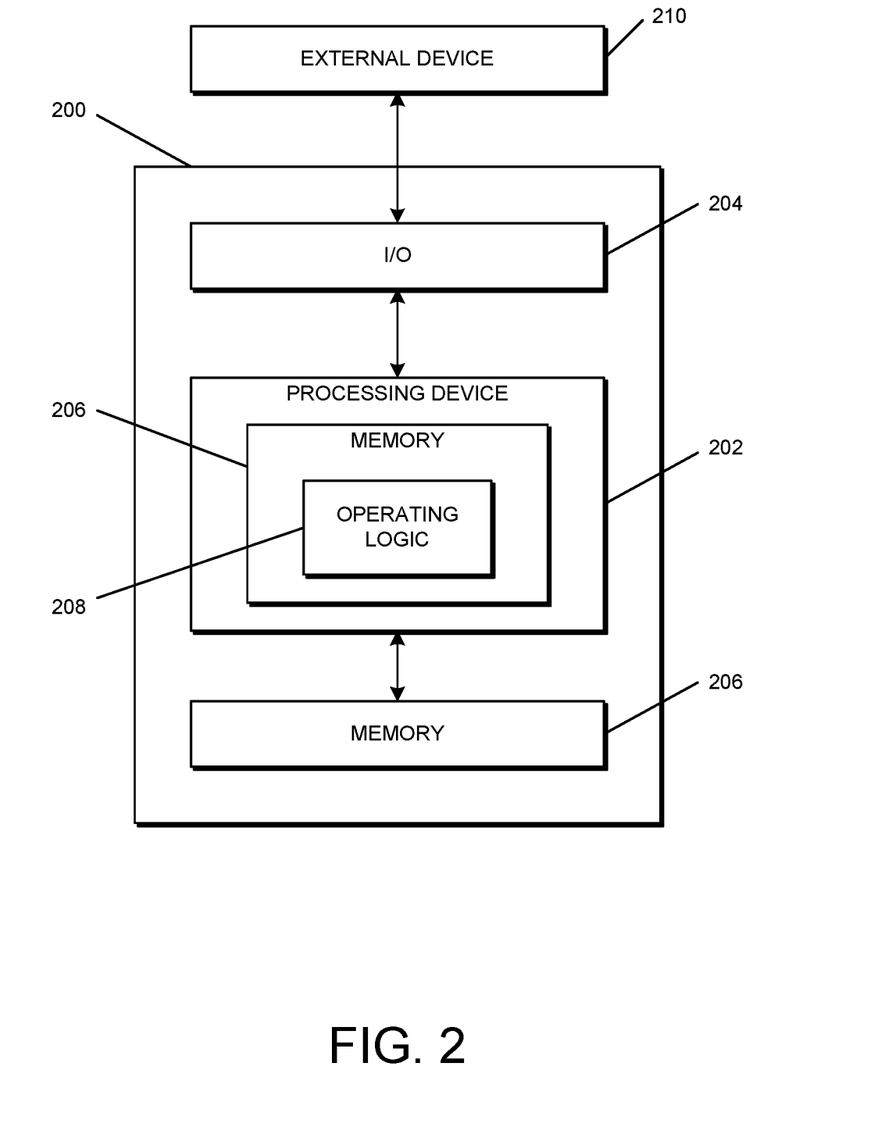
FIG. 2 is a simplified block diagram of at least one embodiment of a computing system.

Referring now to FIG. 2, a simplified block diagram of at least one embodiment of a computing device 200 is shown. The illustrative computing device 200 depicts at least one embodiment of a remote computing system that may be utilized in connection with the remote computing system 108 illustrated in FIG. 1. Depending on the particular embodiment, the computing device 200 may be embodied as a server, desktop computer, laptop computer, tablet computer, notebook, netbook, Ultrabook™, mobile computing device, cellular phone, smartphone, wearable computing device, personal digital assistant, Internet of Things (IoT) device, processing system, router, gateway, and/or any other computing, processing, and/or communication device capable of performing the functions described herein.

The computing device 200 includes a processing device 202 that executes algorithms and/or processes data in accordance with operating logic 208, an input/output device 204 that enables communication between the computing device 200 and one or more external devices 210, and memory 206 which stores, for example, data received from the external device 210 via the input/output device 204.

The input/output device 204 allows the computing device 200 to communicate with the external device 210. For example, the input/output device 204 may include a transceiver, a network adapter, a network card, an interface, one or more communication ports (e.g., a USB port, serial port, parallel port, an analog port, a digital port, VGA, DVI, HDMI, FireWire, CAT 5, or any other type of communication port or interface), and/or other communication circuitry. Communication circuitry of the computing device 200 may be configured to use any one or more communication technologies (e.g., wireless or wired communications) and associated protocols (e.g., Ethernet, Bluetooth® (e.g., BLE), Wi-Fi®, WiMAX, HL7, etc.) to effect such communication depending on the particular computing device 200. The input/output device 204 may include hardware, software, and/or firmware suitable for performing the techniques described herein.

The external device 210 may be any type of device that allows data to be inputted or outputted from the computing device 200. For example, in various embodiments, the external device 210 may be embodied as the hemodialysis control system 102 and/or the holographic system 104. Further, in some embodiments, the external device 210 may be embodied as another computing device, switch, diagnostic tool, controller, printer, display, alarm, peripheral device (e.g., keyboard, mouse, touch screen display, etc.), and/or any other computing, processing, and/or communication device capable of performing the functions described herein. Furthermore, in some embodiments, it should be appreciated that the external device 210 may be integrated into the computing device 200.

The processing device 202 may be embodied as any type of processor(s) capable of performing the functions described herein. In particular, the processing device 202 may be embodied as one or more single or multi-core processors, microcontrollers, or other processor or processing/controlling circuits. For example, in some embodiments, the processing device 202 may include or be embodied as an arithmetic logic unit (ALU), central processing unit (CPU), digital signal processor (DSP), and/or another suitable processor(s). The processing device 202 may be a programmable type, a dedicated hardwired state machine, or a combination thereof. Processing devices 202 with multiple processing units may utilize distributed, pipelined, and/or parallel processing in various embodiments. Further, the processing device 202 may be dedicated to performance of just the operations described herein, or may be utilized in one or more additional applications. In the illustrative embodiment, the processing device 202 is programmable and executes algorithms and/or processes data in accordance with operating logic 208 as defined by programming instructions (such as software or firmware) stored in memory 206. Additionally or alternatively, the operating logic 208 for processing device 202 may be at least partially defined by hardwired logic or other hardware. Further, the processing device 202 may include one or more components of any type suitable to process the signals received from input/output device 204 or from other components or devices and to provide desired output signals. Such components may include digital circuitry, analog circuitry, or a combination thereof.

The memory 206 may be of one or more types of non-transitory computer-readable media, such as a solid-state memory, electromagnetic memory, optical memory, or a combination thereof. Furthermore, the memory 206 may be volatile and/or nonvolatile and, in some embodiments, some or all of the memory 206 may be of a portable type, such as a disk, tape, memory stick, cartridge, and/or other suitable portable memory. In operation, the memory 206 may store various data and software used during operation of the computing device 200 such as operating systems, applications, programs, libraries, and drivers. It should be appreciated that the memory 206 may store data that is manipulated by the operating logic 208 of processing device 202, such as, for example, data representative of signals received from and/or sent to the input/output device 204 in addition to or in lieu of storing programming instructions defining operating logic 208. As shown in FIG. 2, the memory 206 may be included with the processing device 202 and/or coupled to the processing device 202 depending on the particular embodiment. For example, in some embodiments, the processing device 202, the memory 206, and/or other components of the computing device 200 may form a portion of a system-on-a-chip (SoC) and be incorporated on a single integrated circuit chip.

In some embodiments, various components of the computing device 200 (e.g., the processing device 202 and the memory 206) may be communicatively coupled via an input/output subsystem, which may be embodied as circuitry and/or components to facilitate input/output operations with the processing device 202, the memory 206, and other components of the computing device 200. For example, the input/output subsystem may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations.

The computing device 200 may include other or additional components, such as those commonly found in a typical computing device (e.g., various input/output devices and/or other components), in other embodiments. It should be further appreciated that one or more of the components of the computing device 200 described herein may be distributed across multiple computing devices. In other words, the techniques described herein may be employed by a computing system that includes one or more computing devices. Additionally, although only a single processing device 202, I/O device 204, and memory 206 are illustratively shown in FIG. 2, it should be appreciated that a particular computing device 200 may include multiple processing devices 202, I/O devices 204, and/or memories 206 in other embodiments. Further, in some embodiments, more than one external device 210 may be in communication with the computing device 200.

Figure 3:
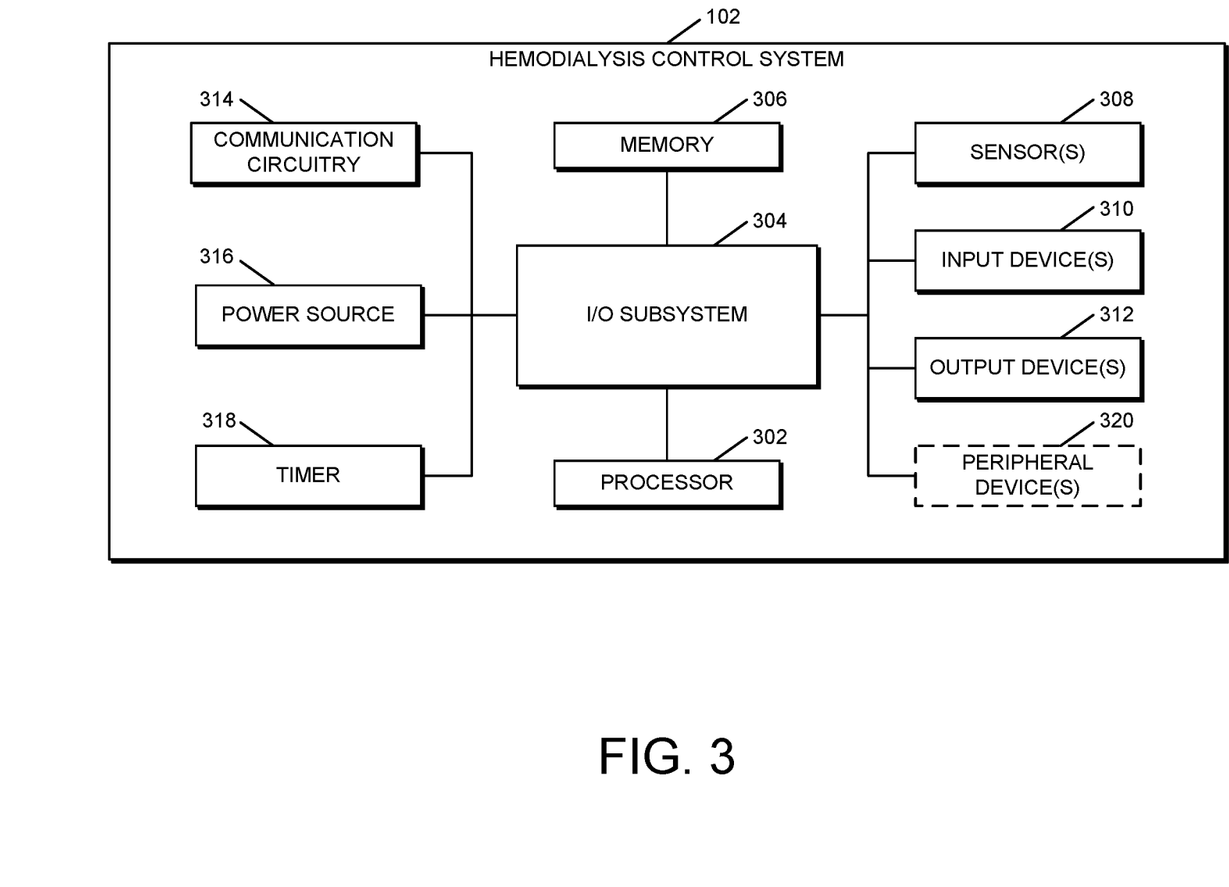
FIG. 3 is a simplified block diagram of at least one embodiment of the hemodialysis control system of FIG. 1.

Referring now to FIG. 3, a simplified block diagram of at least one embodiment of the hemodialysis control system 102 is shown. The illustrative hemodialysis control system 102 includes a processor 302, an input/output ("I/O") subsystem 304, a memory 306, one or more sensors 308, one or more input devices 310, one or more output devices 312, communication circuitry 314, a power source 316, and a timer 318. Further, in some embodiments, the hemodialysis control system 102 may include one or more peripheral devices 320. It should be appreciated that one or more of the components of the hemodialysis control system 102 described herein may be embodied as, or form a portion of, one or more embedded controllers and/or integrated circuits of the hemodialysis machine 110. For example, in some embodiments, the processor 302, the I/O subsystem 304, the memory 306 and/or other components of the hemodialysis control system 102 may be embodied as, or form a portion of, a microcontroller or SoC. Further, depending on the particular embodiment, the components of the hemodialysis control system 102 may be closely positioned to one another or distributed throughout the hemodialysis machine 110 (i.e., separated from one another). As described above, in some embodiments, the hemodialysis control system 102 may be embodied as a control system for a different type of medical device/equipment; however, the control system 102 is described herein primarily in reference to the hemodialysis machine 110 for brevity and clarity of the description.

The processor 302 may be embodied as any type of processor(s) capable of performing the functions described herein. In particular, the processor 302 may be embodied as one or more single or multi-core processors, microcontrollers, or other processor or processing/controlling circuits. For example, in some embodiments, the processor 302 may include or be embodied as an arithmetic logic unit (ALU), central processing unit (CPU), digital signal processor (DSP), and/or another suitable processor(s). The processor 302 may be a programmable type, a dedicated hardwired state machine, or a combination thereof. One or more processors 302 with multiple processing units may utilize distributed, pipelined, and/or parallel processing in various embodiments. Further, the processor 302 may be dedicated to performance of just the operations described herein, or may be utilized in one or more additional applications. In the illustrative embodiment, the processor 302 is of a programmable variety that executes algorithms and/or processes data in accordance with operating logic as defined by programming instructions (such as software or firmware) stored in the memory 306. Additionally or alternatively, the operating logic for the processor 302 may be at least partially defined by hardwired logic or other hardware. Further, the processor 302 may include one or more components of any type suitable to process the signals received from input/output devices or from other components or devices and to provide desired output signals. Such components may include digital circuitry, analog circuitry, or a combination thereof.

The memory 306 may be of one or more types of non-transitory computer-readable media, such as a solid-state memory, electromagnetic memory, optical memory, or a combination thereof. Furthermore, the memory 306 may be volatile and/or nonvolatile and, in some embodiments, some or all of the memory 306 may be of a portable variety, such as a disk, tape, memory stick, cartridge, and/or other suitable portable memory. In operation, the memory 306 may store various data and software used during operation of the hemodialysis control system 102 such as operating systems (e.g., real-time operating systems (RTOS)), applications, programs, libraries, and drivers. The memory 306 is communicatively coupled to the processor 302 via the I/O subsystem 304, which may be embodied as circuitry and/or components to facilitate input/output operations with the processor 302, the memory 306, and other components of the hemodialysis control system 102. For example, the I/O subsystem 304 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. Depending on the particular embodiment, the memory 306 may be included with the processor 302 and/or coupled to the processor 302 depending on the particular embodiment. For example, in some embodiments, the processor 302, the I/O subsystem 304, the memory 306, and/or other components of the hemodialysis control system 102 may form a portion of a system-on-a-chip (SoC) and be incorporated on a single integrated circuit chip.

The sensors 308 are configured to generate sensor data (e.g., by virtue of one or more signals), which may be interpreted by the processor 302 to determine one or more characteristics associated with the hemodialysis control system 102 and/or the associated hemodialysis machine 110. By way of example, the sensors 308 may detect various characteristics of the physical environment of the associated hemodialysis machine 110 (internal and/or external to the machine 110), electrical characteristics of the control system 102 or the associated hemodialysis machine 110, electromagnetic characteristics of the control system 102 or the associated hemodialysis machine 110 or its surroundings, and/or other suitable characteristics. For example, in some embodiments, the sensors 308 may include one or more pressure sensors configured to generate sensor data representative of a corresponding pressure at various locations of the hemodialysis machine 110 (e.g., at an inlet of the dialyzer, an outlet of the dialyzer, etc.). Further, in some embodiments, the sensors 308 may include one or more temperature sensors configured to generate sensor data indicative of a temperature of one or more components of the hemodialysis control system 102, one or more components of the hemodialysis machine 110, fluid being transported via the hemodialysis machine 110, the external environment of the hemodialysis machine 110, and/or otherwise. In some embodiments, the hemodialysis control system 102 may compare sensor data to one or more thresholds to determine whether the corresponding sensor data is within acceptable or expected thresholds/bounds. If not within bounds, the hemodialysis control system 102 may generate an alert message or indication and transmit/output the alert (e.g., via the output devices 312 and/or the communication circuitry 314). For example, in some embodiments, the hemodialysis control system 102 may generate an audible alarm and/or transmit a message to the remote computing system 108 (e.g., an electronic medical records system and/or a nurse station).

It should be appreciated that the sensors 308 may be embodied as, or otherwise include, other sensors in other embodiments. For example, in various embodiments, the sensors 308 may be embodied as, or otherwise include, pressure sensors, environmental sensors, inertial sensors, proximity sensors, optical sensors, electromagnetic sensors, audio sensors, motion sensors, piezoelectric sensors, cameras, fluid/material quality sensors, and/or other types of sensors. It should be appreciated that, in some embodiments, additional and/or alternative sensors 308 other than those described above may be included in the hemodialysis control system 102. Of course, the hemodialysis control system 102 may also include components and/or devices configured to facilitate the use of the sensors 308.

Each of the one or more input devices 310 may be embodied as any type of device or collection of devices capable of accepting or interpreting user input from a user of the hemodialysis control system 102 or, more generally, a user of the hemodialysis machine 110. It should be appreciated that the particular input devices 310 included in the hemodialysis control system 102 may vary depending on the particular embodiment. For example, in the illustrative embodiment, the hemodialysis control system 102 includes a touchscreen display as its primary input/output device. However, it should be appreciated that the hemodialysis control system 102 may include additional or alternative input devices 310 in other embodiments. For example, in various embodiments, the input devices 310 may include one or more touchscreen displays (which may also serve as an output device 312), keypads, keyboards, touchpads, buttons, switches, levers, knobs, wheels, sticks, and/or other types of input devices.

Each of the one or more output devices 312 may be embodied as any type of device or collection of devices capable of outputting information to a user of the hemodialysis control system 102 or, more generally, a user of the hemodialysis machine 110. It should be appreciated that the particular output devices 312 included in the hemodialysis control system 102 may vary depending on the particular embodiment. As indicated above, in the illustrative embodiment, the hemodialysis control system 102 includes a touchscreen display as its primary input/output device. However, it should be appreciated that the hemodialysis control system 102 may include additional or alternative output devices 312 in other embodiments. For example, in various embodiments, the output devices 312 may include one or more touchscreen displays (which may also serve as an input device 310), displays, speakers, indicators, tactile feedback devices, and/or other types of output devices.

The communication circuitry 314 may be embodied as any communication circuitry, transceiver, port, interface, device, or collection thereof, capable of enabling communication between the hemodialysis control system 102 and other devices (e.g., the holographic system 104 and/or the remote computing system 108). The communication circuitry 314 may be configured to use any one or more wired and/or wireless communication technologies and associated protocols (e.g., Ethernet, Bluetooth® (e.g., BLE), Wi-Fi®, WiMAX, HL7, etc.). For example, in some embodiments, the communication circuitry 314 may include a transceiver, network adapter, network card, interface, one or more communication ports (e.g., a USB port, RS-232 or other serial port, parallel port, analog port, digital port, VGA, DVI, HDMI, FireWire, CAT 5, Ethernet (e.g., including PoE), or any other type of communication port or interface), and/or other communication circuitry. As described herein, it should be appreciated that the holographic system 104 may include similar communication circuitry 314 to enable wired and/or wireless communication with the hemodialysis control system 102 via the corresponding communication technology and protocols.

The power source 316 may be embodied as any type of power source capable of powering the hemodialysis control system 102 and, more generally, the hemodialysis machine 110 for sustained, uninterrupted periods of time. For example, in the illustrative embodiment, the power source 316 includes a power supply coupled to line power (e.g., an AC mains power supply). In other embodiments, the power source 316 may be powered by another type of wired power source (e.g., PoE). Further, in some embodiments, the power source 316 may include an independent, untethered, and portable power source configured to supply power to the hemodialysis control system 102. For example, the power source 316 may include one or more batteries, battery packs, capacitors, super capacitors, solar cells, emergency hand cranks, power generators, and/or other power sources.

The timer 318 is configured to track the amount of time that has lapsed using a suitable mechanism (e.g., clock cycles of the processor 302). For example, in some embodiments, the timer 318 may be embodied as a real-time clock. As described below, the timer 318 may be used to determine, for example, the amount of time that has lapsed since a patient's treatment has commenced and/or since another time marker.

The peripheral devices 320 may include any number of additional peripheral or interface devices. For example, in some embodiments, the peripheral devices 320 may include a keyboard, mouse, display, status indicator, diagnostic took, speaker, microphone, and/or one or more other suitable peripheral devices.

It should be appreciated that the hemodialysis control system 102 may include additional or alternative components, such as those commonly found in an embedded control system, for example, in other embodiments. Further, in some embodiments, one or more of the components of the hemodialysis control system 102 described herein may be omitted from the hemodialysis control system 102 of a particular hemodialysis machine 110 and/or other medical device/equipment (e.g., peripheral devices 320).

It should be further appreciated that the holographic system 104 may include features similar to the features of the hemodialysis control system 102 and, therefore, those features have not been repeated herein for brevity and clarity of the description. For example, as indicated above, the holographic system 104 may include communication circuitry similar to the communication circuitry 314 of the hemodialysis control system 102 in order to enable the holographic system 104 to communicate with the hemodialysis control system 102. As described above, in the illustrative embodiment, the holographic system 104 is configured to generate a holographic user interface (e.g., replicating a touchscreen display of the hemodialysis control system 102 in some embodiments), which allows the user to modify settings of the hemodialysis machine 110 without physically touching any component of the hemodialysis machine 110 and, therefore, without having to engage in hand sanitization procedures (e.g., donning/doffing gloves, scrubbing hands, etc.). Accordingly, it should be appreciated that the hemodialysis control system 102 and holographic system 104 are configured to communicate input/output data to one another to allow for such use of the holographic system 104.

In accordance with the healthcare professional's preference or convenience, in circumstances in which the healthcare professional must engage in hand sanitization procedures regardless of her interaction with the hemodialysis machine 110 (e.g., due to physically interacting with the patient), the healthcare professional may simply opt to use the physical controls of the hemodialysis control system 102 (e.g., the input devices 310 and the output devices 312), whereas in other circumstances the healthcare professional may opt to use the non-contact holographic interface of the holographic system 104. In other words, in some embodiments, the same set of functions of the hemodialysis machine 110 may be controlled by a first set of user interface components (e.g., graphical elements) of the hemodialysis control system 102 and/or a second set of user interface components (e.g., graphical elements) of the holographic system 104.

What is claimed is:
1. A system for holographic control of a hemodialysis machine, the system comprising:

a hemodialysis control system of the hemodialysis machine, wherein the hemodialysis control system comprises at least one first processor and at least one first memory comprising a first plurality of instructions stored thereon that, in response to execution by the at least one first processor, causes the hemodialysis control system to provide a first user interface of the hemodialysis machine; and a holographic system communicatively coupled to the hemodialysis control system, wherein the holographic system comprises at least one second processor and at least one second memory comprising a second plurality of instructions stored thereon that, in response to execution by the at least one second processor, causes the holographic system to display a virtual three-dimensional image representative of a second user interface for the hemodialysis machine.

2. The system of claim 1, wherein the first user interface and the second user interface are configured to control a same set of functions of the hemodialysis machine.

3. The system of claim 1, wherein the first user interface comprises a first set of user interface components and the second user interface comprises a second set of user interface components identical to the first set of user interface components.

4. The system of claim 1, wherein the first user interface comprises a first set of user interface components and the second user interface comprises a second set of user interface components different from the first set of user interface components.

5. The system of claim 1, where the holographic system is communicatively coupled to the hemodialysis control system via a wired communication port of the hemodialysis control system.

6. The system of claim 1, wherein the hemodialysis control system comprises an Ethernet port; and
wherein the holographic system is communicatively coupled to the hemodialysis control system via the Ethernet port.

7. The system of claim 1, wherein the hemodialysis control system comprises a USB port; and
wherein the holographic system is communicatively coupled to the hemodialysis control system via the USB port.

8. The system of claim 1, wherein the hemodialysis control system comprises a serial communication port; and
wherein the holographic system is communicatively coupled to the hemodialysis control system via the serial communication port.

9. The system of claim 1, wherein the holographic system is communicatively coupled to the hemodialysis control system via a wireless communication connection directly between the holographic system and the hemodialysis control system.

10. The system of claim 9, wherein the wireless communication connection comprises a Bluetooth communication connection between the holographic system and the hemodialysis control system.

11. The system of claim 1, wherein the hemodialysis control system comprises a touchscreen display that provides the first user interface of the hemodialysis machine.

12. The system of claim 1, further comprising a remote computing system communicatively coupled to the hemodialysis control system via a network and configured to receive patient treatment data from the hemodialysis control system.

13. A system for holographic control of a medical device at risk of touch contamination, the system comprising:
a control system of the medical device, wherein the control system comprises at least one first processor and at least one first memory comprising a first plurality of instructions stored thereon that, in response to execution by the at least one first processor, causes the control system to provide a first user interface of the medical device; and a holographic system communicatively coupled to the control system, wherein the holographic system comprises at least one second processor and at least one second memory comprising a second plurality of instructions stored thereon that, in response to execution by the at least one second processor, causes the holographic system to display a virtual three-dimensional image representative of a second user interface for the medical device.

14. The system of claim 13, wherein the first user interface comprises a first set of user interface components and the second user interface comprises a second set of user interface components identical to the first set of user interface components.

15. The system of claim 13, wherein the first user interface comprises a first set of user interface components and the second user interface comprises a second set of user interface components different from the first set of user interface components.

16. The system of claim 13, wherein the control system comprises at least one of an Ethernet port, a USB port, or a serial communication port; and
wherein the holographic system is communicatively coupled to the control system via one of the at least one of the Ethernet port, the USB port, or the serial communication port.

17. The system of claim 13, wherein the holographic system is communicatively coupled to the control system via a wireless communication connection directly between the holographic system and the control system.

18. The system of claim 13, wherein the first user interface and the second user interface are configured to control a same set of functions of the medical device.

19. The system of claim 13, wherein the medical device assists with hemodialysis of a patient.

* * * * *